United States Patent [19]
Andreiko et al.

[11] Patent Number: 5,139,419
[45] Date of Patent: Aug. 18, 1992

[54] METHOD OF FORMING AN ORTHODONTIC BRACE

[75] Inventors: Craig A. Andreiko, Alta Loma; Terry L. Sterrett, Long Beach, both of Calif.

[73] Assignee: Ormco Corporation, Glendora, Calif.

[21] Appl. No.: 467,162

[22] Filed: Jan. 19, 1990

[51] Int. Cl.⁵ .............................................. A61C 3/00
[52] U.S. Cl. ...................................................... 433/24
[58] Field of Search ........................................... 433/24

[56] References Cited

U.S. PATENT DOCUMENTS

| | | | |
|---|---|---|---|
| 3,660,900 | 5/1972 | Andrews | 433/24 |
| 3,738,005 | 6/1973 | Cohen et al. | 433/24 |
| 3,906,634 | 9/1975 | Aspel | 433/24 |
| 3,949,478 | 4/1976 | Schinhammer | 433/24 |
| 4,014,096 | 3/1977 | Dellinger | 433/24 |
| 5,011,405 | 4/1991 | Lemchen | 433/24 |

Primary Examiner—John J. Wilson
Attorney, Agent, or Firm—Wood, Herron & Evans

[57] ABSTRACT

A model of the teeth in a patient's mouth and a prescription of desired positionings of such teeth are provided by the patient's orthodontist. The contour of the teeth in the patient's mouth is determined, preferably digitally, from the model. Calculations, preferably digital, on the contour and the desired positionings of the patient's teeth are then made to determine the geometry (e.g. grooves) to be provided in brackets for receiving an arch wire to form an orthodontic brace. Such geometry is intended to provide for the disposition of the arched wire on the brackets in a progressive curvature in a horizontal plane and a substantially linear configuration in a vertical plane. The geometry of the brackets is altered (e.g. by cutting grooves in the brackets at individual positions and angles and with particular depths) in accordance with such calculations of the bracket geometry. The brackets may be disposed on the model of the patient's teeth at positions dependent upon such calculations. A mold may be formed of the model of the patient's teeth and the brackets on such teeth. The model and the mold may be shipped to the orthodontist with written instructions for the disposition of the brace on the patient's teeth. Alternatively, an information sheet may be prepared, after the calculation of the bracket geometry, to specify the placement of the brackets on the patient's teeth and the disposition of the arch wire on such brackets. The brackets and the information sheet are sent to the orthodontist.

16 Claims, 5 Drawing Sheets

METHOD OF FORMING AN ORTHODONTIC BRACE

This invention relates to a method of forming an orthodontic brace from a plurality of brackets and an unbent arch wire such that the proper forces are applied by the brace to a patient's teeth to move the patient's teeth into a desired configuration. The invention also relates to an orthodontic brace with such properties.

When the teeth in a patient's mouth are displaced from an even or uniform disposition, such displacements tend to produce problems over an extended period of time. For example, such displacements may produce problems in the patient's gums. These problems may cause the retention of teeth by the patient's gums to become weakened so that the teeth become loose in the patient's mouth. The problem may become so aggravated that the teeth may eventually have to be removed from the patient's mouth.

To prevent the conditions in a patient's mouth from deteriorating, dentists often attempt to reset the positions of the teeth in the patient's mouth. The dentists do this by attaching braces to the patient's teeth and by gradually adjusting the forces applied by the braces to the teeth. These forces act against the teeth in the patient's mouth to move the teeth gradually toward the positions desired by the dentist.

The braces are generally formed by brackets and an arch wire supported in a groove in each of the brackets. Each bracket is adhered to an individual tooth by a pad forming a part of the bracket. The arch wire extends between the brackets on adjacent teeth and applies a force to the teeth to move the teeth toward the positions defined by the patient's orthodontist. Until now, the grooves on the different brackets have been substantially uniform. Because of this, the forces of the arch wire on the teeth have had to be adjusted by bending or otherwise distorting the wires.

The techniques discussed in the previous paragraph have had some beneficial effect. However, they are expensive and imperfect. One reason is that they require a considerable amount of work by the orthodontist to adjust progressively the forces applied against the teeth. Another reason is that the bending and distortion of the arch wire to adjust the forces on the different teeth have been largely on an empirical basis based in large part upon the experience of the orthodontist. As will be appreciated, even an experienced orthodontist is not able to bend or twist an arch wire precisely so that the proper force will be produced on the brackets attached to the individual teeth.

It has been appreciated in the art that it would be desirable to construct the brackets so that the arch wire is planar in an elevational view and is progressively curved in a plan view even after attachment to the brackets and after the disposition in the patient's mouth of the brace formed by the brackets and the arch wire. For example, such a brace has been proposed in U.S. Pat. No. 3,477,128 issued to Lawrence F. Andrews on Nov. 11, 1969 and U.S. Pat. No. 3,660,900 issued to Lawrence F. Andrews on May 9, 1972. In spite of the fact that such a brace has been proposed for such a long time and that considerable work has been performed on providing such a brace, no one has been able as yet to provide such a brace.

The proposals made by Andrews are based upon measurements made in a few skulls. They are not made on an individual basis for each patient. Furthermore, the proposals made by Andrews involve only a limited number of parameters. These parameters are mostly confined to individual characteristics of the grooves in the brackets. As will be appreciated, the proposals made by Andrews are quite crude and would not be sufficient to provide, for the unique parameters represented by the unique configuration and disposition of the teeth in a patient's mouth, a brace in which the arch wire is planar in an elevational view and is progressively curved in a plan view.

The Andrews patents are now twenty (20) years (in one case), or almost twenty (20) years old (in the other case). In that period of time, no one has been able to advance the state of the art beyond the crude state proposed by Andrews. This is true even though a considerable effort has been made, and a significant amount of money has been expended, to advance the state of the art.

This invention provides a method of providing a brace which meets the criteria discussed in the previous paragraph. Specifically, in accordance with the method of this invention, a brace is provided which has a progressive curvature in a plan view plane and a substantially linear configuration in an elevational view and which exerts the proper forces on the teeth in a patient's mouth to move the teeth to a desired configuration predetermined by the patient's orthodontist. By providing such a brace, the method of this invention causes adjustments in the forces applied by the brace on the teeth in a patient's mouth to be minimized.

In one embodiment of the invention, a model of the teeth in a patient's mouth and a prescription of desired positionings of such teeth are provided by the patient's orthodontist. The contour of the teeth in the patient's mouth is determined, preferably digitally, from the model.

Calculations, preferably digital, on the contour and the desired positionings of the patient's teeth are then made to determine the geometry to be provided in brackets for receiving an arch wire to form an orthodontic brace. Such geometry is intended to provide for the disposition of the arched wire on the brackets in a progressive curvature in a plan view and a substantially linear configuration in an elevational view. The geometry of the brackets is altered in accordance with such calculations of the bracket geometry.

The geometry of the brackets may be altered in a number of different ways to provide the desired results. For example, the length, depth, width and positioning of the groove in the bracket may be individual to each bracket. Furthermore, if there are any rounded corners or curved surfaces to be provided in the grooves in each bracket, these are also determined on an individual basis. The height of each bracket and the angle of inclination of such bracket may also be individually determined. The width of each bracket and the curvature of the surface adhered on the bracket to the tooth may also be individually determined.

The brackets may be disposed on the model of the patient's teeth at positions dependent upon such calculations. A mold may be formed of the model of the patient's teeth and the brackets on such teeth. The model and the mold may be shipped to the orthodontist with written instructions for the disposition of the brace on the patient's teeth.

Alternatively, an information sheet may be prepared, after the calculation of the bracket geometry and the formation of the brackets, to specify the placement of the brackets on the patient's teeth and the disposition of the arch wire on such brackets. The brackets and the information sheet are sent to the orthodontist. The orthodontist is able, on the basis of the information in the sheet, to dispose the arch wire on the brackets to form the brace and to dispose the brace in the patient's mouth with the arch wire in a progressively curved disposition in a planar view and in a linear configuration in an elevational view.

In the drawings

FIGS. 10(a)-10(g) are side elevational views of brackets with different slot configurations;

Figure 8:
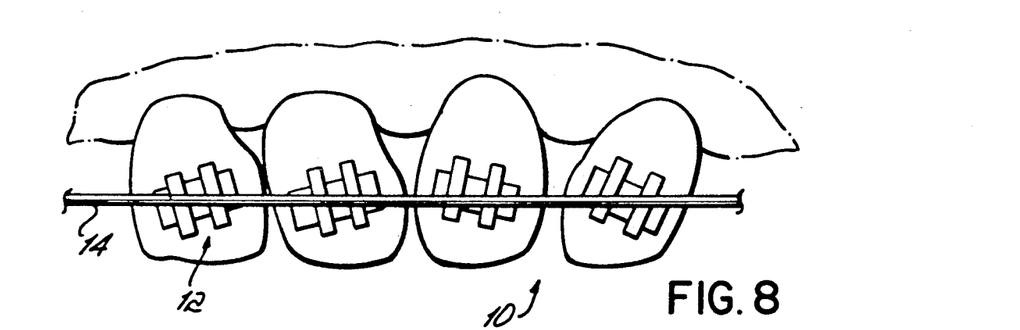
FIG. 8 is a side elevational view schematically illustrating a plurality of teeth and the disposition on such teeth of a brace made in accordance with the method of this invention.
Figure 9:
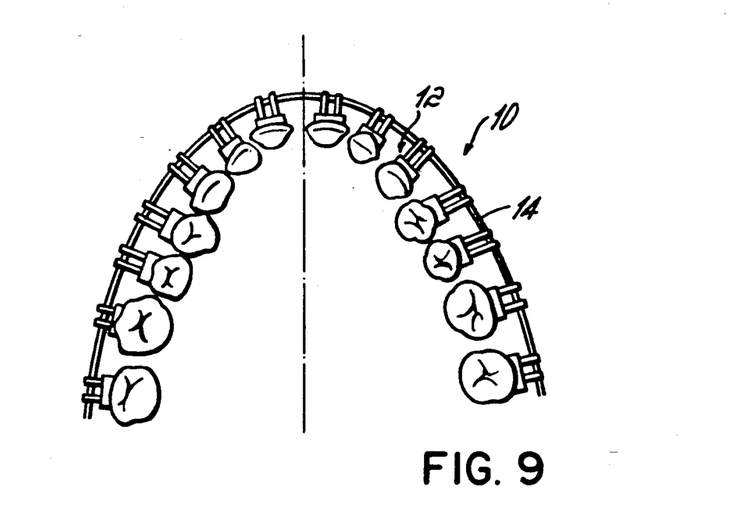
FIG. 9 is a schematic plan view illustrating the disposition of the brace on the teeth in the patient's mouth.

The method of this invention provides an optimal formation of a brace generally indicated at 10 in FIGS. 8 and 9. The brace 10 includes brackets generally indicated at 12 and an arch wire 14 supported by the brackets. The arch wire 14 is disposed in an arched configuration having a progressive curvature when viewed on a plan basis (FIG. 9) and having a linear configuration when viewed on an elevational basis (FIG. 8). In this way, there are no discontinuities in the arch wire 14 when viewed either on a planar or an elevational basis.

Figure 6A:
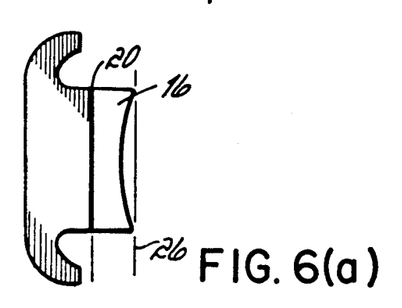
FIGS. 6(a) through 6(e) are side elevational views illustrating how an individual bracket in the brace can be provided with different types of geometry in accordance with the method represented by the flow charts of FIGS. 1 and 2.
Figures 6B, 6C, 6D, 6E:
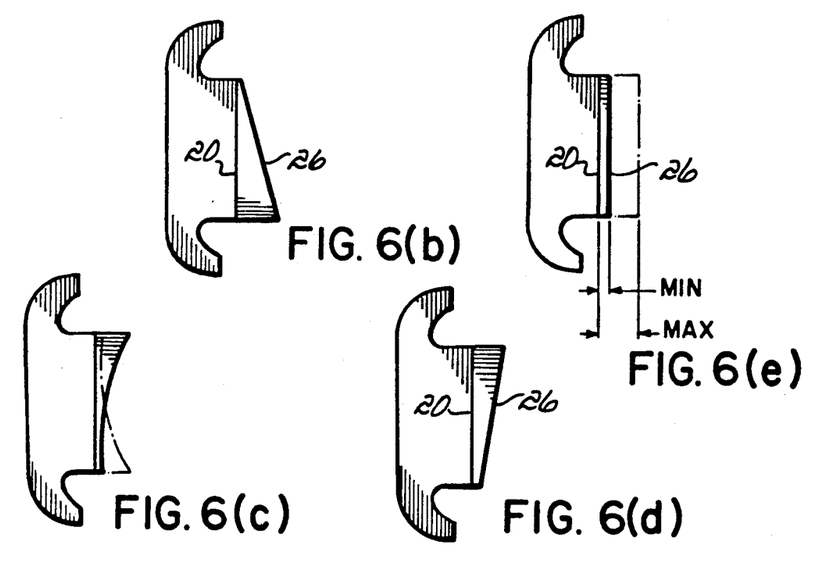
Figure 7A:
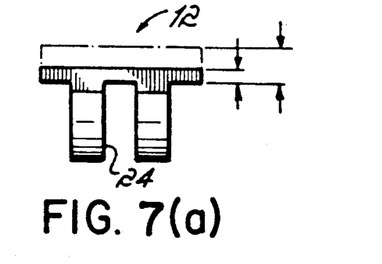
FIG. 7(a) through 7(e) are top plan views further illustrating how an individual bracket in the brace can be provided with different types of qeometry, other than those shown in FIGS. 6(a) through 6(e), in accordance with the methods represented by the flow charts of FIGS. 1 and 2.
Figure 7B:
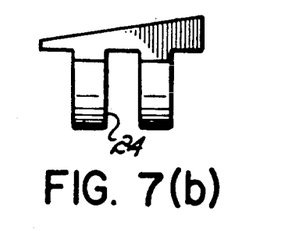
Figure 7C:
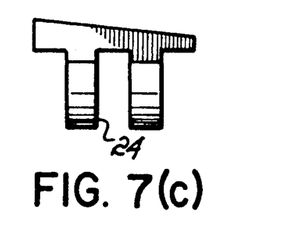
Figure 7D:
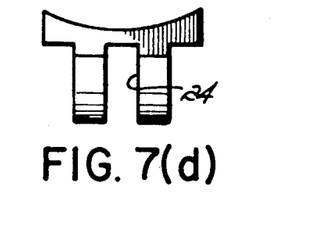
Figure 7E:
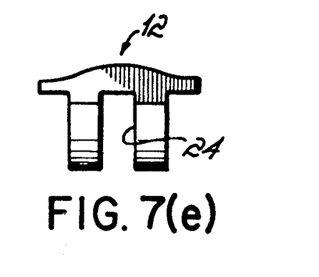

Each bracket 12 includes a pad 16 and a support member 18 (FIG. 6). The pads 16 and the support members 18 may be constructed in a manner disclosed and claimed in Pat. No. 4,068,379 issued to Frank R. Miller, Craig A. Andrieko and Kenneth R. Premo on Jan. 17, 1978, and Pat. No. 4,165,561 issued to Frank R. Miller, Craig A. Andreiko and Kenneth R. Premo on Aug. 28, 1979. The pads 16 and the support members 18 are made from a suitable material such as stainless steel. Stainless steel is desirable because it will not corrode in the patient's mouth. The pads 16 may preferably be in the form of a mesh.

Each of the pads 16 is bonded at one surface, as by an adhering glue 20, to the supporting member 18 and the other surface of the pad is bonded to one of the patient's teeth. Alternatively, the bracket may be constructed with an integral pad or bonding base. The support members 18 are provided with grooves 24 in an outer surface 26 to receive the arch wire 14. The grooves 24 are provided with, lengths, depths, and widths, and are angled, to receive the arch wire 14 such that the arch wire exerts forces on the patient's teeth to move the teeth to a configuration predetermined by the patient's orthodontist. The different lengths and depths and angles of the grooves 24 are schematically shown in FIGS. 10(a)-10(g). The different angles of the grooves 24 are schematically shown in FIGS. 11(a)-11(c).

To perform the method constituting this invention, a patient's orthodontist provides a model 30 (FIG. 12) of the teeth in the patient's mouth as such teeth actually appear, from the standpoint of positioning and configuration, in the patient's mouth. This may be provided by having the patient bite into a plasticizable material to define a female mold. This mold is then used to form the model. The orthodontist also provides a prescription of a desired positioning and configuration of the teeth in the patient's mouth. The dentist supplies the mold and the prescription to a laboratory, which then performs the steps in the method of this invention.

Figure 12:
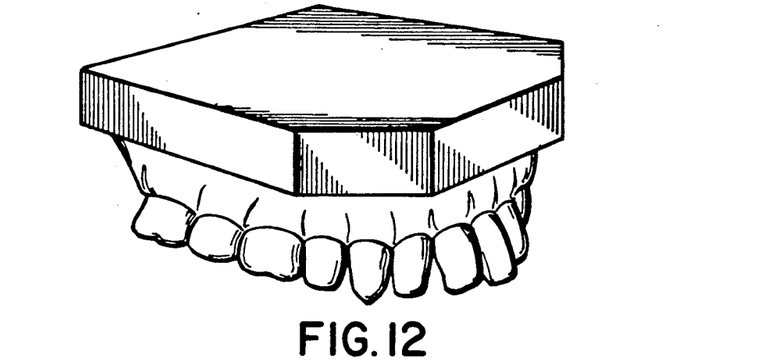
FIG. 12 is a perspective view of a model of the positioning and configuration of the teeth in a patient's mouth before the teeth are reset to the positions predetermined by the patient's orthodontist.

The laboratory first determines the contour of each of the teeth in the model 30. This contour may constitute the thickness of the tooth at progressive positions in the vertical direction between the tip of the tooth and the patient's gum. The contour of each tooth in the model 30 may constitute a mesio-distal profile. This represents the thickness of each tooth at a median position between the opposite lateral ends of the tooth. Alternatively, additional contours may be determined for each tooth in the model at positions displaced from the median position. The contours are preferably determined on a digital basis to facilitate the processing of this information with other information determined in the laboratory.

Figure 1:
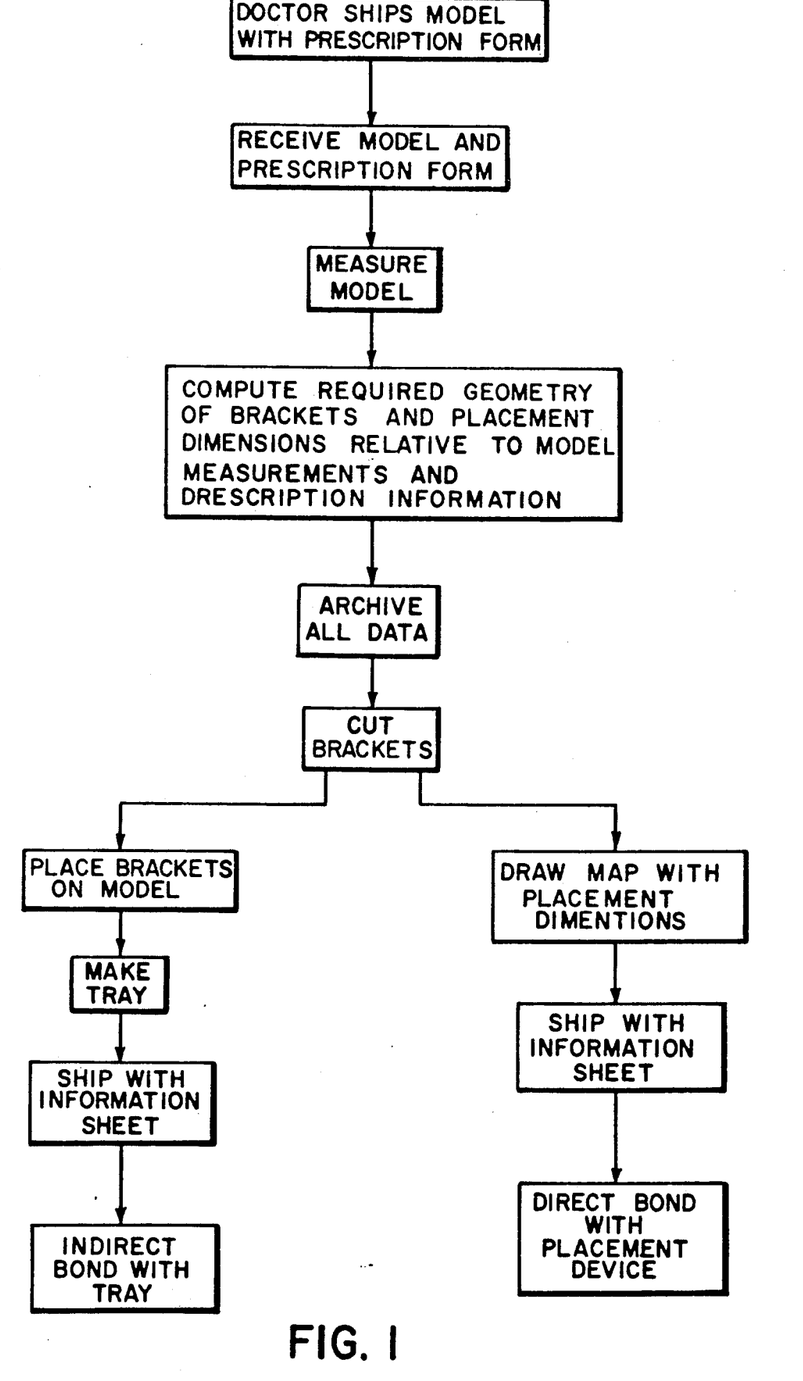
FIG. 1 is a schematic flow chart of one embodiment of a method constituting this invention for forming a brace including an arch wire which is progressively curved in a plan view and is substantially linear in an elevational view.
Figure 2:
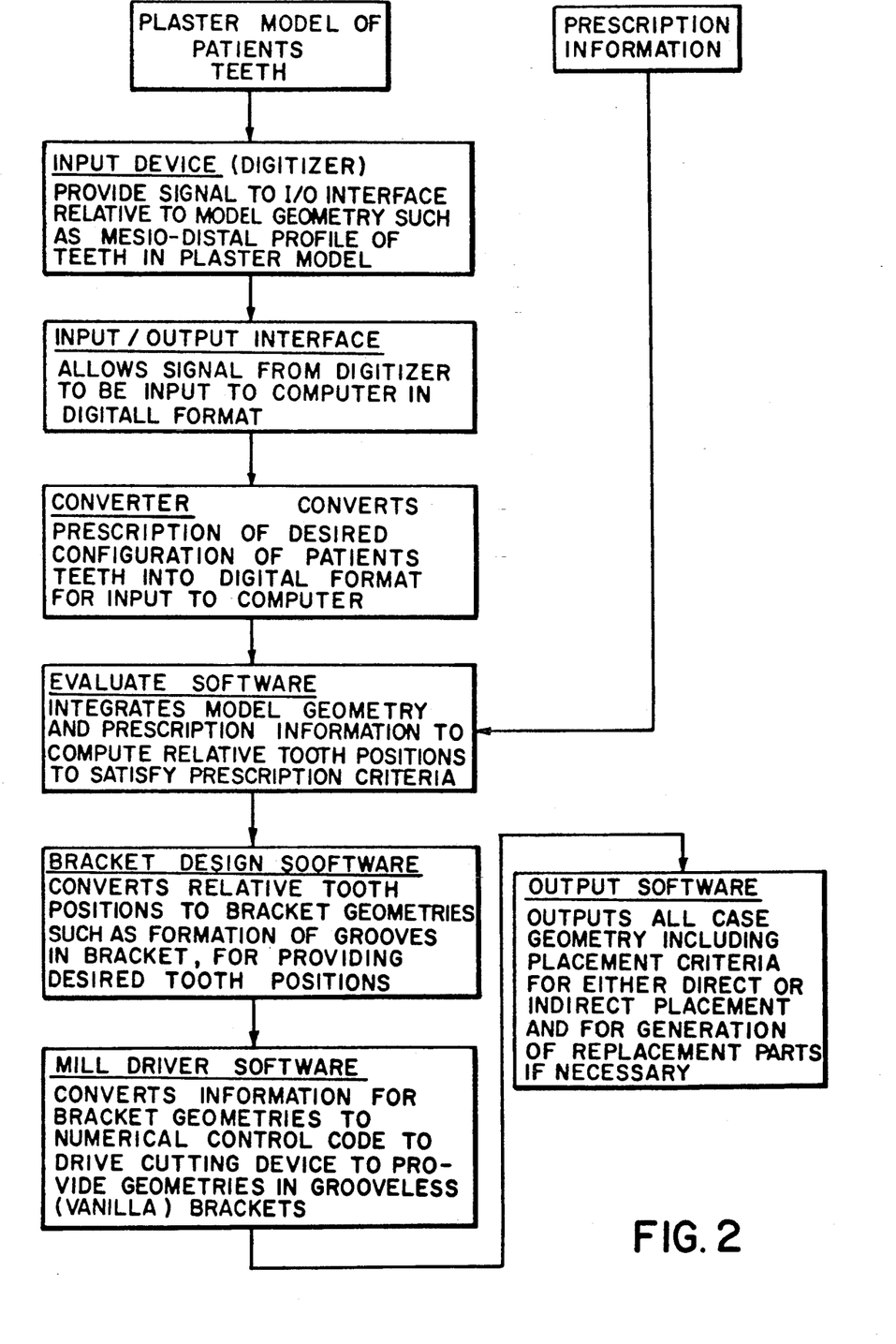
FIG. 2 is a schematic flow chart, in additional detail, of the method shown in FIG. 1.
Figure 3:
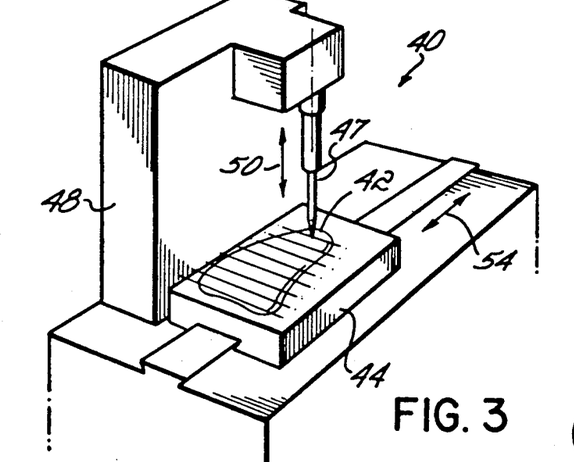
FIG. 3 is a schematic view of equipment which may be used to perform one of the steps in the method shown in FIGS. 1 and 2.
Figure 4:
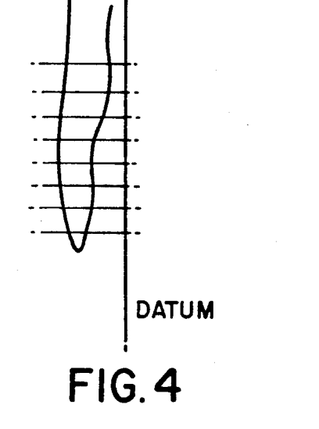
FIG. 4 is a schematic view of a tooth and illustrates how the equipment shown in FIG. 3 performs the step in the method shown in FIGS. 1 and 2.
Figure 5:
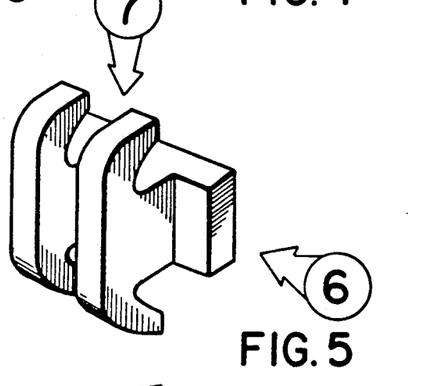
FIG. 5 is a fragmentary schematic view of a brace formed from a plurality of brackets and an arch wire and schematically illustrates a pair of brackets and a portion of the arch wire in the brace.

FIG. 3 illustrates apparatus, generally indicated at 40, for determining the contour of each tooth in the model 30, one of these teeth being illustrated schematically at 42 in FIG. 4. As shown in FIG. 3, the apparatus 30 includes a platform 44 for supporting the model 30 in a manner so that any selected tooth in the model 30 can rest on the platform. A probe 46 is supported on a stanchion 48 for movement in the vertical direction. The probe 46 is accordingly movable downwardly in FIG. 3 to contact the tooth whose contour is being determined. This is indicated by an arrow 50 in FIG. 3. The platform 44 is movable horizontally to probe the contour of this tooth at progressive positions on the tooth. This is indicated schematically by arrows 54 in FIG. 3.

It will be appreciated that the apparatus shown in FIG. 3 and described in the previous paragraph constitutes only one type of apparatus which may be used to determine the contour of the patient's teeth. For example, apparatus employing lasers, sonic elements or elements employing machine vision may also be used to determine the contour of the patient's teeth.

The prescription of the desired positionings and configuration of the patient's teeth are used to compute the geometry of the brackets. This information may relate to several different parameters. For example, the information may relate to various parameters defining the grooves 24 in the support members 18. These parameters may include the angle of the groove 24 in the support member 18, the lateral position of the groove in the outer surface 26, the width of the groove and the depth of the groove. The geometry of the groove 24 may also involve other parameters such as curvatures in the groove or configurations, other than linear, in the walls of the grooves to provide the brackets with the desired parameters.

The geometry of the brackets 12 may also involve other parameters such as variations in the distance between the surfaces 20 and 26 on the support member 18 in an elevational view. This is schematically shown in FIG. 6(e). The minimum distance is shown in solid lines in FIG. 6(e) and the maximum distance is shown in broken lines in FIG. 6(a). The geometry of the brackets 12 may also involve additional parameters such as variations in the angle of the surface 20 relative to the surface 26 of the support member 18 on an elevational basis. Different angles of the surface 20 relative to the surface 26 of the support member 24 are schematically illustrated in FIGS. 6(b) and 6(d).

Other parameters involved in the geometry may be the width of each support member 18 to have the width correspond substantially to the width of the teeth to which the bracket including such support member is to be bonded. Furthermore as, indicated in FIG. 6(a) and by solid and broken lines in FIG. 6(c), the pad 16 may be provided with a curvature in an elevational view corresponding to the curvature of the tooth to which the pad is to be bonded.

FIG. 7 indicates how particular parameters of the brackets 12 may be varied in the plan view. For example, FIG. 7(a) indicates how the thickness of the bracket may be varied in the plan direction. FIGS. 7(b) and 7(c) indicate examples in a plan view of different angles in the brackets 12. FIGS. 7(d) and 7(e) illustrate different curvatures of the brackets 12 in a plan view.

Figure 10A:
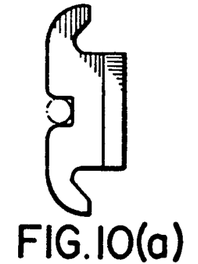
Figure 10B:
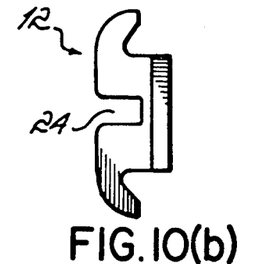
Figure 10C:
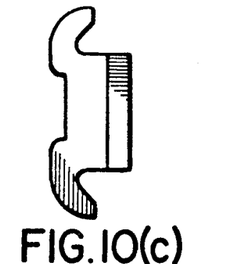
Figure 10D:
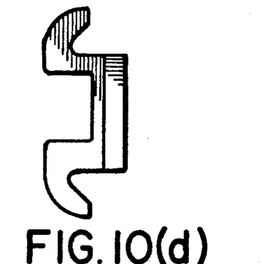
Figure 10E:
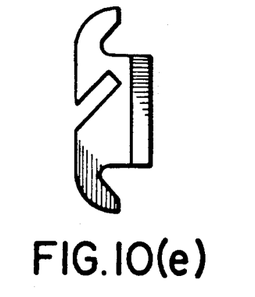
Figure 10F:
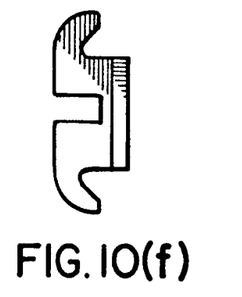
Figure 11A:
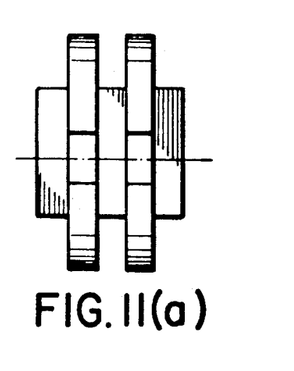
FIGS. 11(a)-11(c) are front elevational views of brackets with different angles of the slots in the brackets.
Figure 11B:
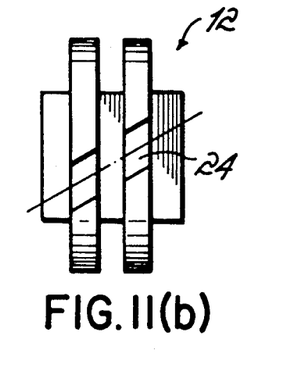
Figure 11C:
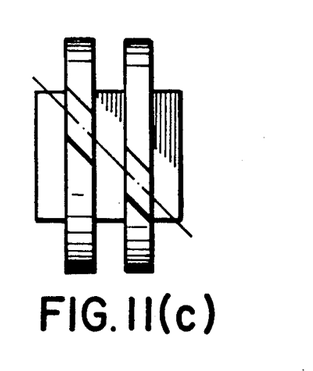

FIGS. 10(a)-10(g) illustrate different configurations of the brackets in elevation. For example, FIGS. 10(a) and 10(b) illustrate different depths of the slot 24 in the bracket 12. FIGS. 10(c) and 10(d) illustrate a different height of the slot 24 than FIGS. 10(a) and 10(b) and further illustrate different depths of the slot for such different height. FIGS. 10(e)-10(g) illustrate different angles at which the slot 24 can be disposed in the bracket 12. FIGS. 11(a)-11(c) are front elevational views showing different angles of the slot 24 in the bracket 12.

The different parameters are provided with characteristics to provide the arch wire 14 with a progressive curvature in a plan view and a substantially linear configuration in an elevational view when the arch wire 14 is attached to the support members 18. The computations also indicate how the brackets 12 should be disposed on the patient's teeth from vertical, lateral and rotational standpoints.

It will be appreciated that the teeth in the patient's mouth may have some rebound after the arch wire 14 and the brackets 12 have been removed from the patient's mouth. It may accordingly be desirable to provide the arch wire 14 with a curvature representing some overshoot in the positioning of the patient's teeth beyond the optimal positioning of the teeth in the patient's mouth. This is considered to be within the scope of the invention. As used in the claims, the term "desired positioning of the teeth in a patient's mouth" is intended to include such an overshoot if the curvature of the arch wire 14 is designed to provide such an overshoot.

The computations discussed in the previous paragraph are then stored in a memory. The computations are also used to cut the grooves 24 in the support member 18 and to provide the support member and the pad 16 with the preferred geometry discussed in the previous paragraphs. In one embodiment of the method constituting this invention, the brackets are disposed on the teeth in the model in accordance with such computations and are adhered to the teeth on the model with a glue providing for a relatively easy removal of the brackets from the teeth. A female mold is then made of the model with the brackets properly positioned on the model.

The model with the brackets properly positioned on the teeth is then shipped to the orthodontist. An information sheet indicating the proper disposition of the brackets 12 on the teeth in the patient's mouth is also shipped to the orthodontist to instruct the orthodontist how to dispose the brackets 12 on the patient's teeth and how to install the arch wire 14 on the brackets. A duplicate information sheet may be retained by the laboratory for future reference. The female mold may also be shipped to the orthodontist. This may provide the orthodontist with an opportunity of making a female mold may also be shipped o the orthodontist. This may provide the orthodontist with an opportunity of making a female mold after the positioning of the brackets 12 on the teeth and comparing this female mold with the mold shipped to the dentist by the laboratory.

Alternatively, a map may be prepared by the laboratory This may shows the proper disposition of the brackets on the teeth in the patient's mouth. The laboratory may ship this map, the brackets 12, the arch wire 14 and the information sheet to the orthodontist.

The method of this invention offers certain advantages over the prior art. It provides for the formation of brackets with proper geometry to provide for the disposition of the bracket properly on the teeth and the disposition o the arch wire in the brackets such that the arch wire has a progressive curvature in a plan view and a substantially linear configuration in an elevational view. Furthermore, the geometry of the brackets is such that the arch wire exerts a for e on the teeth in the patient's mouth to move the teeth to a desired configuration prescribed by the orthodontist. The brackets are formed with the proper configuration automatically and without human intervention.

The brace 10 of this invention also has certain important advantages. It is formed on an individual basis for each patient to displace the teeth in that patient's mouth to a configuration and positioning prescribed b the patient's orthodontist. The brace 10 is formed on this individual basis by determining through calculations the geometry to be provided for the different brackets 12 in the brace. This geometry is such that the arch wire 14 has a progressive curvature in a plan view and s substantially linear disposition in an elevational view even after the arch wire is attached to the brackets.

It will be appreciated that the method of this invention may be used to form a brace only for a limited number of successive teeth in a patient's mouth. For example, the method of this invention may be used to form a brace only for the incisors or for the teeth between or including the biscuspids.

As will be appreciated, data systems are used in this invention to determine the contour of the teeth in the model on an individual basis. The application Such data processing systems may be any personal computer now available on the market. Data processing apparatus is also used to determine the geometry of the brackets 12. Such data processing processing equipment may include CAD/CAM systems now commercially available from a number of companies including Daisy Systems, Sun Microsystems and Apollo Computer (now a part of Hewlett-Packard Company).

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

We claim:

1. A method of forming for a dental patient an orthodontic brace from a plurality of brackets and an each wire disposed in a progressive curvature in a plan view and a substantially linear configuration in an elevational view, including the steps of:
   determining the thickness of each tooth at progressive positions on the tooth in the vertical direction between the tip of the tooth and the patient's gum,
   providing a desired disposition of the teeth in the patient's mouth,
   digitally calculating the geometry to be provided individually for each bracket to receive the arch wire in the progressive curvature in the plan view and the substantially linear configuration in h elevational view, such digital calculations being provided on the basis of the thickness of each tooth at progressive positions on the tooth between the tip of the tooth and the patient's gum and the desired disposition of eh teeth in the patient's mouth,
   digitally calculating the disposition of each bracket on the associated tooth, and
   providing the individual brackets with the digitally calculated parameters and the digitally calculated disposition of the brackets of the associated teeth to receive the arch wite in the progressive curvature in the plan view and the substantially linear configuration in the elevational view.

2. A method as set forth in claim 1 including the step of:
   disposing the arch wire on the brackets in the progressive curvature the plan view and in the substantially linear configuration in the elevational view in accordance with the parameters provided for the individual brackets.

3. A method as set forth in claim 2 wherein the digitally calculated geometry is provided for each individual bracket by cutting a groove in such racket at a particular angle in the bracket and to a particular depth in the bracket and at a particular position in the bracket.

4. A method as set forth in claim 1 wherein a model is provided of the teeth in the patient's mouth and
the thickness of each tooth in the patient's mouth at the progressive positions of such tooth in the vertical direction between the tip of such tooth and the patient's gum is digitally determined from the model.

5. A method as set forth in claim 1 wherein
a map is made of the dispositions of the brackets on the patient's teeth for use by the orthodontist in forming the brace and disposing the brace in the patient's mouth.

6. A method as set forth in claim 1 wherein
the thickness of each tooth is determined at progressive positions on the tooth in the vertical direction in a mesio-distal profile between the tip of the tooth and the patient's gum.

7. A method of forming for a dental patient an orthodontic brace from a plurality of brackets and an arch wire disposed in a progressive curvature in a plan view and a substantially linear configuration in an elevational view, including the steps of:
   providing a model of the teeth in the patient's mouth,
   providing a prescription of the desired positionings of the teeth in the patient's mouth,
   digitally determining parameters, including the mesio-distal profile between the tip of the tooth and the patient's gum, of each of the teeth in the patient's mouth from the model at progressive vertical positions on the model of each of the teeth in the patient's mouth,
   using the digitally determined parameters, including the mesio-distal profile between the tip of each tooth and the patient's gum, of each of the teeth in the patient's mouth and the prescription of the desired positionings of each of the teeth in the patient'mouth in digitally calculating the geometries of the brackets, in accordance with the optimal tooth positions in the patient's mouth, required to obtain the progressive curvature of the arch wire in the plan view and the substantially linear configuration of the arch wire in the elevational view, and
   controlling the operation of numerically controlled machinery, in accordance with the calculations of the geometries of the brackets, to provide the brackets with such geometric parameters.

8. A method as set forth in claim 7 wherein
the digital determinations of the parameters, including the mesio-distal profile between the tip of each tooth and the patient's gum, of each of the teeth in the patient's mouth are provided for a plurality of different positions on each tooth,
the prescription of the desired configuration of the teeth in the patient's mouth is in a digital form, and
the calculations of the optimal positions of the geometries of the brackets in the patient's mouth are in a digital form on the basis of the digital determinations for the different positions on each tooth.

9. A method as set forth in claim 8 wherein
the disposition of each tooth on the associated bracket is digitally determined by using the digitally determined parameters including the mesio-distal profile between the tip of each tooth and the patient's gum and the prescription of the desired propositioning of each of the teeth in the patients s mouth,
the arched wire is attached to the brackets in accordance with the geometries provided in the brackets, the brackets are attached to the model of the teeth in the patient's mouth in accordance with the calculations of the disposition of the brackets on the associated teeth, and a mold is made of the model of the teeth in the patient's mouth with the brackets and the arch wire on the teeth.

10. A method as set forth in claim 8, including the steps of:

calculating the preferred disposition of the brackets on the teeth, and forming a map showing the disposition of the brackets on the teeth and the disposition of the arch wire on the brackets in accordance with the calculations indicating such disposition and showing the disposition of the brackets on the teeth in the patient's mouth.

11. A method as set forth in claim 8 including the step of providing written instructions of use by the patient's orthodontist in attaching the arch wire to the brackets and in disposing the brackets and the arch wire in the patient's mouth.

12. A method of forming for a dental patient an orthodontic brace from a plurality of brackets and an arch wire disposed in a progressive curvature in a plan view and a substantially linear configuration in an elevational view, including the steps of:

providing a model of the teeth in the patient's mouth, providing a prescription of the desired disposition of the teeth in the patient's mouth, digitally determining from the model the contour, including the mesio-distal thickness between the tip of each tooth and the patient's gum, of each of the teeth in the patient's mouth, digitally calculating from such determinations the geometry, including a groove to be provided in the brackets and the placement to be made of the brackets on the patient's teeth, in accordance with the prescription of the desired positionings of the teeth in the patient's mouth and the contour, including the mesio-distal thickness, of each of the teeth in the patient's mouth, to obtain the disposition of the arched write on the brackets in the progressive curvature in the plan view and the substantially linear configuration in the elevational view, and cutting the brackets in accordance with the cuts calculated to be made in eh brackets.

13. A method as set forth in claim 12, including the steps of disposing the brackets and the arch wire on the model of the teeth in the patient's mouth, and forming a model of the model of the teeth in the patient's mouth and the brackets and the arch wire on the teeth.

14. A method as set forth in claim 13 including the step of providing written instructions as to how the brace is to be disposed in the patient's mouth.

15. A method as set forth in claim 12, including the step of providing a map identifying the different brackets and showing the placement of the brackets on the patient's teeth.

16. A method as set forth in claim 12 wherein the mesio-distal profile is digitally determined for each tooth at a number of different positions on such tooth and wherein the digital calculations are made from such determinations of the geometry to be provided in the brackets and the placement to be made of the brackets on the patient's teeth in accordance with the prescription of the desired positionings of the teeth in the patient's mouth.

* * * * *

UNITED STATES PATENT AND TRADEMARK OFFICE
CERTIFICATE OF CORRECTION

PATENT NO. : 5,139,419

DATED : August 18, 1992

INVENTOR(S) : Craig A. Andreiko et al.

Page 1 of 2

It is certified that error appears in the above-identified patent and that said Letters Patent is hereby corrected as shown below:

Column 4, line 1, "4,068,379" should be --4,068,399--.

Column 6, lines 33-37, please delete "This may provide the orthodontist with an opportunity of making a female mold may also be shipped o the orthodontist.".

Column 6, line 49, "o" should be --of--.

Column 6, line 53, "for e" should be --force--.

Column 6, line 61, "b" should be --by--.

Column 6, line 66, "s" should be --a--.

Column 7, line 7, please insert --processing-- after "data" and before "system".

Column 7, line 9, please delete "The application".

Column 7, line 27, "each" should be --arch--.

Column 7, line 39, "h" should be --the--.

Column 7, line 44, "eh" should be --the--.

Column 7, line 49, "of" (second occurrence) should be --on--.

Column 7, line 50, "wite" should be --wire--.

Column 7, line 56, please insert --in-- after "curvature" and before "the".

UNITED STATES PATENT AND TRADEMARK OFFICE
CERTIFICATE OF CORRECTION

PATENT NO. : 5,139,419

DATED : August 18, 1992

INVENTOR(S) : Craig A. Andreiko et al.

It is certified that error appears in the above-identified patent and that said Letters Patent is hereby corrected as shown below:

Column 7, line 63, "racket" should be --bracket--.

Column 8, line 35, "patient'" should be --patient's--.

Column 8, line 64, "propositioning" should be --positionings--.

Column 10, line 11, "eh" should be --the--.

Column 10, line 16, "model" should be --mold--.

Signed and Sealed this

Twenty-first Day of June, 1994

*Attest:*

BRUCE LEHMAN

*Attesting Officer*     *Commissioner of Patents and Trademarks*